US010722545B2

(12) United States Patent
Kariman

(10) Patent No.: US 10,722,545 B2
(45) Date of Patent: Jul. 28, 2020

(54) COMPOUND AND METHOD FOR TREATMENT OF MOVEMENT DISORDERS

(71) Applicant: Alexander Kariman, Rockville, MD (US)

(72) Inventor: Alexander Kariman, Rockville, MD (US)

( * ) Notice: Subject to any disclaimer, the term of this patent is extended or adjusted under 35 U.S.C. 154(b) by 164 days.

(21) Appl. No.: 15/859,692

(22) Filed: Jan. 1, 2018

(65) Prior Publication Data
US 2019/0201463 A1    Jul. 4, 2019

(51) Int. Cl.
| | | |
|---|---|---|
| *A61K 36/00* | (2006.01) | |
| *A61K 36/185* | (2006.01) | |
| *A61K 47/44* | (2017.01) | |
| *A61K 9/48* | (2006.01) | |
| *A61K 9/20* | (2006.01) | |
| *A61K 9/00* | (2006.01) | |
| *A61P 25/32* | (2006.01) | |
| *A61P 25/16* | (2006.01) | |
| *A61K 31/01* | (2006.01) | |
| *A61K 31/355* | (2006.01) | |
| *A61K 31/56* | (2006.01) | |

(52) U.S. Cl.
CPC .......... *A61K 36/185* (2013.01); *A61K 9/0078* (2013.01); *A61K 9/2009* (2013.01); *A61K 9/4825* (2013.01); *A61K 9/4858* (2013.01); *A61K 47/44* (2013.01); *A61P 25/16* (2018.01); *A61P 25/32* (2018.01); *A61K 31/01* (2013.01); *A61K 31/355* (2013.01); *A61K 31/56* (2013.01); *A61K 2300/00* (2013.01)

(58) Field of Classification Search
CPC .................................................. A61K 36/00
USPC ....................................................... 424/725
See application file for complete search history.

(56) References Cited

U.S. PATENT DOCUMENTS

| | | | |
|---|---|---|---|
| 7,968,594 B2 | 6/2011 | Guy | |
| 8,628,796 B2 | 1/2014 | Kottayil | |
| 8,808,734 B2 * | 8/2014 | Winnicki | A61K 9/127 424/450 |
| 8,980,940 B2 | 3/2015 | Rossi | |
| 9,205,063 B2 | 12/2015 | Guy | |
| 2004/0018151 A1 | 1/2004 | Abood | |
| 2006/0135599 A1 | 6/2006 | Symonds | |
| 2006/0167084 A1 | 7/2006 | Dudley | |
| 2008/0175902 A1 | 7/2008 | Zajicek | |
| 2014/0228438 A1 | 8/2014 | Iuvone | |

OTHER PUBLICATIONS

Paolicelli, D., Direnzo, V., Mann, A., D'Onghia, M., Tortorella, C., & Zoccolella, S. Long-Term Data of Efficacy, Safety, and Tolerability in a Real-Life Setting of THC/CBD Oromucosal Spray—Treated Multiple Sclerosis Patients. The Journal of Clinical Pharmacology, 2015, 56(7), pp. 845-851.
Hoggart, B., Ratcliffe, S., Ehler, E., Simpson, K. H., Hovorka, J., Lejčko, J., . . . Serpell, M. A multicentre, open-label, follow-on study to assess the long-term maintenance of effect, tolerance and safety of THC/CBD oromucosal spray in the management of neuropathic pain. J Neurol, 2015, 262(1), pp. 27-40.
Serpell, M., Ratcliffe, S., Hovorka, J., Schofield, M., Taylor, L., Lauder, H., & Ehler, E. A double-blind, randomized, placebo-controlled, parallel group study of THC/CBD spray in peripheral neuropathic pain treatment. Eur J Pain, 2014, 18(7), pp. 999-1012.
Brady, C. M., Dasgupta, R., Dalton, C., Wiseman, O. J., Berkley, K. J., & Fowler, C. J. An open-label pilot study of cannabis-based extracts for bladder dysfunction in advanced multiple sclerosis. Mult Scler., 2004, 10(4), pp. 425-433.
Collin, C., Davies, P., Mutiboko, I. K., & Ratcliffe, S. Randomized controlled trial of cannabis-based medicine in spasticity caused by multiple sclerosis. Eur J Neurol, 2007, 14(3), pp. 290-296.
Johnson, J. R., Lossignol, D., Burnell-Nugent, M., & Fallon, M. T. An open-label extension study to investigate the long-term safety and tolerability of THC/CBD oromucosal spray and oromucosal THC spray in patients with terminal cancer-related pain refractory to strong opioid analgesics. J Pain Symptom Manage., 2013, 46(2), pp. 207-218.
Russo, E., & Guy, G. W. A tale of two cannabinoids: the therapeutic rationale for combining tetrahydrocannabinol and cannabidiol. Med Hypotheses, 2006, 66(2), pp. 234-246.
Rog, D. J., Nurmikko, T. J., Friede, T., & Young, C. A. Randomized, controlled trial of cannabis-based medicine in central pain in multiple sclerosis. Neurology., 2005, 65(6), pp. 812-819.
Koppel, B. S., Brust, J. C., Fife, T., Bronstein, J., Youssof, S., Gronseth, G., & Gloss, D. Systematic review: efficacy and safety of medical marijuana in selected neurologic disorders: report of the Guideline Development Subcommittee of the American Academy of Neurology. Neurology, 2014, 82(17), pp. 1556-1563.
Leussink V. I., Husseini, L., Warnke, C., Broussalis, E., Hartung, H.-P., & Kieseier, B. C. Symptomatic therapy in multiple sclerosis: the role of cannabinoids in treating spasticity. Ther Adv Neurol Disord., 2012, 5(5), pp. 255-266.
Jamontt, J. M., Molleman, A., Pertwee, R. G., & Parsons, M. E. The effects of Δ9-tetrahydrocannabinol and cannabidiol alone and in combination on damage, inflammation and in vitro motility disturbances in rat colitis. Br J Pharmacol, 2010, 160(3), pp. 712-723.
Karniol, I. G., Shirakawa, I., Kasinski, N., Pfeferman, A., & Carlini, E. A. Cannabidiol interferes with the affects of Δ9-tetrahydrocannabinol in man. European Journal of Pharmacology, 1974, 28(1), pp. 172-177.
Peertwee, R. G. The diverse CB1 and CB2 receptor pharmacology of three plant cannabinoids: Δ9-tetrahydrocannabinol, cannabidiol and Δ9-tetrahydrocannabivarin. British Pharmacological Society, 2008, 153(2), pp. 199-215.
Kluger, B., Triolo, P., Jones, W., & Jankovic, J. The Therapeutic Potential of Cannabinoids for Movement Disorders. Mov Disord., 2015, 30(3), pp. 313-327.

\* cited by examiner

*Primary Examiner* — Michael V Meller

(57) ABSTRACT

The disclosed invention generally relates to pharmaceutical compounds and methods for treating and/or preventing diseases and disorders that often manifest in hyper and/or hypokinetic movements symptoms, as well as the method of administering therapeutically-effective amount of a pharmaceutical compound containing cannabinoids to subjects in need of treatment. The disclosed invention further relates to cannabinoid pharmaceutical compounds where said compound contains at least some non-cannabinoid components.

2 Claims, 4 Drawing Sheets

| Huntington's Disease | | |
|---|---|---|
| 3NP rats | Arvanil (CB1 and TRPV1 receptor agonist) significantly reduced hyperkinetic activity in lesioned animals and increased glutamate in the globus pallidus. It also reduced ambulation and other activity in both lesioned and control animals. | de Lago E, Urbani P, Ramos JA, Di Marzo V, Fernandez-Ruiz J. Arvanil, a hybrid endocannabinoid and vanilloid compound, behaves as an antihyperkinetic agent in a rat model of Huntington's disease. Brain Res. 2005;1050(1–2):210–216. |
| 3NP rats | UCM707 (AEA transport inhibitor) reduced hyperkinetic activity and increased both glutamate and GABA levels in the globus pallidus. | de Lago E, Fernandez-Ruiz J, Ortega-Gutierrez S, et al. UCM707, an inhibitor of the anandamide uptake, behaves as a symptom control agent in models of Huntington's disease and multiple sclerosis, but fails to delay/arrest the progression of different motor-related disorders. Eur Neuropsychopharmacol. 2006;16(1):7–18. |
| 3NP rats | AM404 (AEA transport inhibitor) attenuated motor hyperactivity, reduced ambulatory activity and improved toxin-induced GABA and dopamine deficits. | Lastres-Becker I, Hansen HH, Berrendero F, et al. Alleviation of motor hyperactivity and neurochemical deficits by endocannabinoid uptake inhibition in a rat model of Huntington's disease. Synapse. 2002;44(1):23–35. |
| 3NP rats | AM404 (AEA transport inhibitor) reduced hyperkinesia and was reversed by capsazepine (VR1 antagonist) but not rimonabant (CB1 antagonist). VDM11 (CB reuptake inhibitor) and AM374 (CB hydrolysis inhibitor) did not reduce chorea. Capsaicin (VR1 agonist) and CP55,940 (CB1 and CB2 receptor agonist) reduced hyperkinesia but only capsaicin improved basal ganglia GABA and dopamine deficits. | Lastres-Becker I, de Miguel R, De Petrocellis L, Makriyannis A, Di Marzo V, Fernández-Ruiz J. Compounds acting at the endocannabinoid and/or endovanilloid systems reduce hyperkinesia in a rat model of Huntington's disease. Journal of Neurochemistry. 2003;84(5):1097–109. |
| R6/1 transgenic mice | HU210 (CB1 and CB2 agonist) and THC did not affect motor deterioration and HU210 treatment was associated with seizures and increased ubiquinated aggregates in the striatum. | Dowie MJ, Howard ML, Nicholson LFB, Faull RLM, Hannan AJ, Glass M. Behavioural and molecular consequences of chronic cannabinoid treatment in Huntington's disease transgenic mice. Neuroscience. 2010;170:324–336. |

Figure 3

COMPOUND AND METHOD FOR TREATMENT OF MOVEMENT DISORDERS

FIELD OF THE INVENTION

The present invention relates to pharmaceutical compounds and methods for treating and/or preventing diseases and disorders that often manifest in hyper and hypokinetic movements symptoms, such as Huntington's Disease (HD) and Parkinson's Disease (PD), and to pharmaceutical compounds and methods for treating and/or preventing symptoms associated with said diseases and disorders.

BACKGROUND OF THE INVENTION

Cannabinoid (CB) components of marijuana are known to exert behavioral and psychotropic effects but also to possess therapeutic properties including analgesia, ocular hypotension, and antiemesis. CBs-based medications are now being used for treatment of a wide range of medical conditions, including neuropathic pain, pain related to cancer and trauma, spasticity associated with multiple sclerosis, fibromyalgia, and others. This invention generally relates to treatment and/or prevention of hyper and hypokinetic movement symptoms associated with cannabinoid-responsive diseases and disorders in subjects in need thereof, as well as the method of administering therapeutically-effective amount of a pharmaceutical compound containing CBs.

CBs are a group of chemicals known to activate CB receptors in cells. These chemicals, which are found in cannabis plants, are also produced endogenously in humans and other animals, these are termed endocannabinoids. Synthetic CBs are chemicals with similar structures to plant CBs or endocannabinoids. Plant cannabinoids can also be isolated such that they are "essentially pure" compounds. These isolated CBs are essentially free of the other naturally occurring compounds, such as, other minor CBs and molecules such as terpenes.

The methods and compounds of the proposed invention are intended for treatment of multiple diseases, disorders, and conditions such as: HD; Wilson's Disease; Sydenham's Chorea; Chorea Gravidarum; Autosomal Dominant Neurogenetic Syndrome; Huntington's Disease-Like Syndrome; Prion Disease; Spinocerebellar Ataxias; Neuroacanthocytosis; Dentatorubral-Pallidoluysian Atrophy; Brain Iron Accumulation Disorders; Friedreich's Ataxia; Mitochondrial Disease; Rett Syndrome; Cerebrovascular Disease; Pediatric Autoimmune Neuropsychiatric Disorders Associated with Streptococcal Infections (PANDAS); Levodopa-Induced Dyskinesia (LID), anti-convulsants and anti-psychotics drugs-related symptoms; Systemic Lupus Erythematosus; Antiphospholipid Syndrome; Tourette Syndrome (TS); Thyrotoxicosis; Polycythaemia Rubra Vera; Spongiform Encephalopathies; Coeliac Disease; PD; metabolic and endocrine-related diseases and disorders; athetosis-related to damage or degeneration of basal ganglia; minor tranquilizers and alcohol withdrawal syndromes; symptoms or side effects associated with anti-retroviral therapy, chemotherapy and radiation therapy.

Other diseases, disorders and conditions that cause athetosis, dystonia, tremors, tics, myoclonus, stereotypies, dyskinesia, restless legs syndrome, and Periodic Limb Movement Disorder (PLMD) are also contemplated by the invention. In addition, the methods of the invention may be used to alleviate, or relief symptoms or side effects associated with anti-retroviral therapy, chemotherapy, radiation therapy, and treatment of chemical withdrawal. Certain diseases and disorders are briefly outlined below, and the possible mechanisms of CB action are exemplified with treatment of certain diseases that cause hyperkinetic or hypokinetic movement symptoms.

Most hyperkinetic and hypokinetic movement disorders are caused by a dysfunction of basal ganglia-thalamocortical loops. Central CB receptors are located in large quantities in the output nuclei of the basal ganglia (globus pallidus, substantia nigra pars reticulata). It suggests that they could be involved in the regulation of motor activity. There is evidence that endogenous CB transmission plays a role in the manipulation of other transmitter systems within the basal ganglia by increasing GABAergic transmission, inhibiting glutamate release and affecting dopaminergic uptake.

In recent years a limited number of clinical trials in humans demonstrated that CBs might be useful in the treatment of movement disorders. It has been suggested that an endogenous CB tone participates in the control of movements and, therefore, the central Endo-Cannabinoid System (ECS) might play a role in the pathophysiology of these diseases. There is also limited evidence that CBs are of therapeutic value in the treatment of tics in TS, the reduction of LID in PD and some forms of tremor and dystonia. There is also evidence that CBs are useful in the treatment of chorea in HD and hypokinetic parkinsonian syndromes. Currently, treatments of these and similar diseases are focused on relieving symptoms and preventing complications because there is no curative therapy. Medical interventions include: physical therapy, immunosuppressive medication, hormone replacement therapy, blood transfusions (if blood is affected), anti-inflammatory medication, pain medication, and others.

Preclinical research in animal models of several movement disorders have shown variable evidence for symptomatic benefits but more consistently suggest potential neuroprotective effects in several animal models of PD and HD. Clinical observations and clinical trials of CB-based therapies suggest a possible benefit of CBs for tics.

The primary CB receptor subtypes are CB receptors type 1 (CB1) and type 2 (CB2). CB1 receptors are highly expressed in the Central Nervous System (CNS), especially the basal ganglia, and also identified in almost all peripheral tissues and cell types. CB2 receptors are expressed primarily in the immune system, where they modulate inflammation, but are also expressed in the CNS, particularly in neurons within the dorsal vagal motor nucleus, the nucleus ambiguous, the spinal trigeminal nucleus, and microglia. CB2 receptors were also found in the basal ganglia and studies suggest that impairment of these receptors may be associated with dyskinesia. While most actions of CBs are related to CB1 and CB2 receptors, other receptor types have been described, including the Transient Receptor Potential Vanilloid type 1 (TRPV1) cation channel, the GTP-binding Protein-coupled Receptor GPR55, the abnormal-CBD receptor, and the Peroxisome-Proliferator-Activated Receptor (PPAR). (Kluger, Triolo, Jones, & Jankovic, 2015)

Endogenously produced CBs (eCBs) are lipophilic compounds that demonstrate varying degrees of affinity for G-protein coupled CB receptors and include anandamide and 2-arachidonoglycerol. eCBs primarily function through retrograde signaling, wherein post-synaptic activity leads to eCB production and release with backward transmission across the synapse to depress presynaptic neurotransmitter release. The ECS may also support synapse formation and neurogenesis. Within the basal ganglia, eCBs and CB1 receptors tend to increase GABAergic and inhibit glutamatergic transmission. eCBs also tend to inhibit dopamine release through GABAergic mechanisms. eCBs are not stored and are quickly degraded after exerting a transient and localized effect. Removal of eCBs from the extracellular space occurs through cellular uptake and metabolism with anandamide degraded primarily by Fatty Acid Amide Hydrolysis (FAAH) and 2-AG degraded by monoacylglycerol lipase. (Kluger, Triolo, Jones, & Jankovic, 2015)

According to Kluger, Triolo, Jones, and Jankovic, and as further suggested in the preclinical studies shown in FIG. 3, a number of PD and HD studies in animal models suggest that CB-based therapies may reduce neurodegeneration and reduce hyperkinetic activity. (Kluger, Triolo, Jones, & Jankovic, 2015) The U.S. Pat. No. 6,630,507 referenced herein, provides a list of CBs useful in certain neurodegenerative diseases such as PD, Alzheimer's Disease (AD), and dementia caused by human immunodeficiency virus. A number of recent studies conclude that CBs may offer neuroprotection through both receptor-mediated and receptor-independent mechanisms. According to Sagredo, et al., CBs are capable of reducing oxidative damage by acting as scavengers of Reactive Oxygen Species (ROS) and enhancing endogenous antioxidant defenses. (Sagredo, et al., 2007) Certain CBs, such as CBD and THC may appear to exhibit this property independent of CB1 and CB2 receptor modulation. These CBs also exhibit anti-inflammatory effects by inhibiting reactive microglia and cytokine release. There is also evidence that CB1 agonists reduce excitotoxicity by suppressing glutamatergic activity, subsequent calcium ion influx, and nitric oxide production. (Romero & Orgado, 2009)

Experimental animal models indicate that HD is associated with early and widespread reductions in the ECS, particularly CB1 receptors in the striatum. CB1 receptors mediate brain-derived neurotrophic factor expression and CB1 receptor loss is associated with exacerbation of symptoms, neuropathology, and molecular pathology in the striatum. Moreover, CBs-based therapies generally show neuroprotection in several animal models through both CB receptor mediated and independent effects. (Kluger, Triolo, Jones, & Jankovic, 2015) Therapeutic studies of CB-based agents in HD animal models suggest that CB1 and endovanilloid receptor agonists, and anandamide reuptake inhibitors are capable of alleviating hyperkinesia. This therapeutic potential is likely to be realized in early phases of HD because of progressive loss of CB1 receptors in advanced stages. (Lastres-Becker, et al., 2001)

Experimental models of PD show increased ECS activity in the basal ganglia, including increased CB1 mRNA levels, CB1 activity, anandamide levels, and decreased CB clearance. These changes appear to be associated with movement suppression and may be reversed by chronic levodopa treatment. Importantly, many CBs demonstrate neuroprotective effects in several models of PD. These effects appear to be mediated by both CB receptor dependent and independent mechanisms including antioxidant effects, reduced microglia activation, and modulation of glial-neuron interactions. (Kluger, Triolo, Jones, & Jankovic, 2015) Animal studies further suggest that CBs may improve motor symptoms of PD and LID. CB1 agonists inhibit basal ganglia dopamine release and are therefore could be ineffective in alleviating PD motor symptoms. Indeed, CB1 agonists have been shown to exacerbate bradykinesia in 1-methyl-4-phenyl-1,2,3,6-tetrahydropyridine (MPTP)-lesioned primates. (Meschler, Howlett, & Madras, 2001)

However, CB1 agonists have also been reported to improve motor impairments, possibly through nondopaminergic mechanisms including interactions with adenosine A2A receptors. Studies of CB1 antagonists are more consistent in improving motor symptoms without increasing dyskinesias. These effects appear to involve nondopaminergic mechanisms including enhanced striatal glutamate release and may be greater in animals with more severe striatonigral degeneration. (Kluger, Triolo, Jones, & Jankovic, 2015)

It is conceivable that CB1 agonists also reduce overactivity of the globus pallidus interna and improve dystonia by reducing GABA reuptake. In support of this idea, the CB1 and CB2 agonist WIN55,212-2 produces antidystonic effects in a mutant hamster model of dystonia, increases the antidystonic efficacy of benzodiazepines and is reversed by rimonabant, a selective CB1 antagonist. Animal models suggest that CBs may reduce Multiple Scleroses (MS)-related tremor, an effect that appears to be selectively mediated by CB1 receptors.

Case reports of smoked cannabis, oral THC, and case series of smoked cannabis suggest that CBs may be beneficial for tics in patients with TS. Similarly, a survey of 64 TS patients found that 17 (27%) had tried marijuana and 14 of them (82%) found it helpful for tics and behavioral disturbances. (Müller-Vahl, Kolbe, Schneider, & Emrich, 1998) There is also evidence suggesting that CBs may be effective for ataxia, myoclonus or restless legs syndrome. Two case reports suggest ataxia (in combination with spasticity) in MS may improve following smoked cannabis or oral THC. (Meinck, Schonle, & Conrad, 1989)

It was discovered that glutamate toxicity could be prevented to some extent by isolated or synthetic THC or CBD. (Hampson, Grimaldi, Axelrod, & Wink, 1998) The CBs were also tested in vitro on neuronal cultures exposed to glutamate. CBD and other CBs were examined as neuroprotectants in rat cortical neuron cultures exposed to toxic levels of the neurotransmitter, glutamate.

According to Hampson, et al., the psychotropic CB receptor agonist delta 9-THC and a non-psychoactive constituent of marijuana—CBD, both reduced the n-methyl-d-aspartic acid (NMDA) and α-amino-3-hydroxy-5-methyl-4-isoxazole propionic acid (AMPA) receptors, as well as kainate receptor mediated neurotoxicity. Neuroprotection was not affected by CB receptor antagonist, indicating a CB receptor-independent mechanism of action. (Hampson, et al., 2000)

Glutamate toxicity can be reduced by antioxidants. Using cyclic voltammetry and a fenton reaction-based system, it was demonstrated that CBD, THC and other CBs are potent antioxidants. As evidence that CBs can act as antioxidants in neuronal cultures, CBD was demonstrated to reduce hydroperoxide toxicity in neurons. In a head to head trial of the abilities of various antioxidants to prevent glutamate toxicity, CBD was superior to both alpha-tocopherol and ascorbate in protective capacity. The preliminary studies in a rat model of focal cerebral ischemia suggest that CBD may be at least as effective in vivo as seen in these in vitro studies. (Hampson, et al., 2000)

The example illustrated in FIG. 2, incorporated herein by reference, compares the oxidation potentials of CBs and the antioxidant Butylated Hydroxytoluene (BHT). Effect of CBD and THC on dihydrorhodamine oxidation. CBs were compared with BHT for their ability to prevent tert-butyl hydroperoxide-induced oxidation of dihydrorhodamine. This experiment was repeated four times with essentially the same results. (Hampson, Grimaldi, Axelrod, & Wink, 1998)

A study by Formukong, Evans, & Evans was undertaken to determine the analgesic and anti-inflammatory activity of various CBs and CB pre-cursors. Oral administration of CBD was found to be the most effective at inhibition of phenyl-p-benzoquinone-induced writhing in mice. THC and CBN were found to be least effective at reducing analgesia and inflammation. (Formukong, Evans, & Evans, 1988) Another study undertaken by Hampson, Grimaldi, Axelrod, & Wink, as exemplified in FIG. 1, incorporated herein by reference, compares the oxidation potentials of CBs and the antioxidant BHT. (Hampson, Grimaldi, Axelrod, & Wink, 1998)

Further, certain anecdotic evidence suggests that CB-containing plant extracts are demonstrating higher efficacy in treatment of some neurodegenerative diseases than essentially pure CBs. Specifically, CB-containing plant extracts comprising, as a predominant CB, THC and CBD—particularly effective in the retardation of neural degeneration.

Several pharmaceutical products exist which contain either phytocannabinoids (natural) or synthetic CBs. For example, dronabinol (Marinol) is the International Nonproprietary Name (INN) for an encapsulated THC product which has been used therapeutically as an appetite stimulant, antiemetic, and analgesic, either as an inhalant or as an oral drug. Also, nabilone (Cesamet) is a synthetic analog of dronabinol (Marinol), while Sativex is a CB extract oral spray containing THC, and other CBs that are used to treat neuropathic pain, spasticity, nausea associated with cancer chemotherapy, and stimulate appetite in HIV patients. Further, rimonabant (marketed under various tradenames) is a selective cannabinoid receptor antagonist used as an anti-obesity drug and as a smoking cessation. Several other cannabinoid-containing products exist.

Thus, considering the therapeutic effect of compounds containing CBs, especially (—)-$\Delta^9$-trans-THC, there is a continuing need for improving existing CB-containing products as well as a need for new products and delivery systems containing CBs, especially in the pharmaceutical field.

The use of cannabis as a medicine has long been known and during the 19$^{th}$ century preparations of cannabis were recommended as a hypnotic sedative which were useful for the treatment of hysteria, delirium, epilepsy, nervous insomnia, migraine, pain and dysmenorrhea. Until recently the administration of cannabis to a patient was mainly achieved by preparation of cannabis by decoction in ethanol, which could then be swallowed or by the patient inhaling the vapors of cannabis by smoking the dried plant material.

It is important to note that side effects, as well as therapeutic effects, vary depending on the CBs, concentration of CBs, or ratio of CBs in formulations. Smoking cannabis has been associated with lung cancer risk, although oral administration is also problematic due to deposition of CBs into fatty tissue, from which they are released slowly, causing variability in plasma concentrations. (Kluger, Triolo, Jones, & Jankovic, 2015) There is also an important risk of abuse with marijuana and cannabis-based drugs due to the psychotropic effect of THC. (Haberstick, et al., 2014) Studies of marijuana outside of the medical context estimate 9% of persons using cannabis may become addicted and experience symptoms of withdrawal after quitting the drug. (Warner, Kessler, Hughes, Anthony, & Nelson, 1995) These, along with legal issues, are some of the main difficulties today in treating patients with natural CBs. Inconsistent drug delivery systems (smoking, oral sprays, inhalers, and others), inconsistent compounds due to the natural variances of CBs, inherent instability of certain CBs, as well as abuse potential due to the psychotropic effect, are some of the areas that this invention aims to overcome by providing a standardized, medical-grade CB-based pharmaceutical and delivery system for effective treatment of movement disorders with minimal psychotropic effect and therefore abuse potential.

Recent methods have sought to find new ways to deliver CBs to a patient including those which bypass the stomach and the associated first pass effect of the liver which can remove up to 90% of the active ingested dose and avoid the patient having to inhale unhealthy tars and associated carcinogens into their lungs. Such dosage forms include administering the CBs to the sublingual or buccal mucosae, inhalation of a CB vapor by vaporization or nebulization, enemas or solid dosage forms such as gels, capsules, tablets, pastilles and lozenges.

To attain the required purity of isolated CBs, up to at least 95% by total weight, consistent ratio of CBs in the formulation, attain pharmaceutical-grade stability of active CBs, effective and consistent delivery system for treating multiple conditions, as well as therapeutically-effective treatment methods—requires a know-how that is proposed in this document. However, there is existing prior art, such as patents, published patent applications, academic work, and other, that is related but distinct from the proposed invention.

The U.S. Pat. No. 7,449,589, referenced herein, demonstrates one of many processes for purifying (-)-$\Delta$9-trans-tetrahydrocannabinol and shows various cannabinoid compounds, including THC, CBD, and CBN. The THC reportedly has at least eight individual isomers of which (-)-$\Delta$9-trans-tetrahydrocannabinol ((-)-$\Delta$9-trans-THC) is the main and most active isomer. Although $\Delta$8-tetrahydrocannabinol has similar activity as (-)-$\Delta$9-trans-THC, it is only approximately 75% as potent and also tends to degrade to other compounds including CBN. (U.S. Pat. No. 7,449,589 B2, 2004)

The U.S. Pat. No. 8,628,796, referenced herein, discloses an encapsulated THC composition, including (-)-$\Delta$9-trans-THC purportedly having improved stability. The disclosure emphasizes that the stability can be improved by including bases (e.g., amines) in the formulation. In addition, the stability of the compositions disclosed is best preserved by storing the compositions in a sealed container, such as in a capsule, and under refrigerated conditions. Specifically, the disclosure asserts that one embodiment of the invention described therein overcomes the deficiencies of prior art oral dosage forms containing (-)-$\Delta$9-trans-THC by utilizing hard gelatin capsules, instead of soft gelatin capsules. As stated in the disclosure, unlike soft gelatin capsules, hard gelatin capsules do not contain glycerol—a major cause of instability for the active (-)-$\Delta$9-trans-THC pharmaceutical ingredient. The disclosure purports to provide a stable product, such as one that does not degrade to an unacceptable extent during the desired shelf-life of the dosage form. (U.S. Pat. No. 8,628,796 B2, 2005)

The U.S. Pat. No. 7,968,594, referenced herein, discloses the invention that relates to treatment of cancer related pain and constipation. The subject in need is administered a combination of CBD and delta-9-THC in a predefined ratio by weight of approximately 1:1 of CBD to THC. (U.S. Pat. No. 7,968,594 B2, 2005)

The U.S. Pat. No. 9,205,063, also published as the U.S. Pat. No. 8,673,368, referenced herein, discloses in one aspect, a method that relates to use of one or more CB-containing plant extracts consisting essentially of an extract of *Cannabis sativa* obtained by supercritical or subcritical extraction with CO2; and where said extract is used in the prevention or treatment of neural degeneration, wherein the one or more CB-containing plant extracts comprise a CB-containing fraction, consisting essentially of the major CB, a minor CB, and one or more other CBs, and a non-CB containing fraction. (U.S. Pat. No. 9,205,063 B2, 2014) (U.S. Pat. No. 8,673,368 B2, 2007)

The U.S. Pat. Application No. 20,140,228,438, referenced herein, discloses the invention that relates to CBs for use in the prevention or treatment of neurodegenerative diseases or disorders. Preferably, the CBs are cannabichromene (CBC) cannabidivarin (CBDV) and/or cannabidivarin acid (CB-DVA). More preferably, the neurodegenerative disease or disorder to be prevented or treated is Alzheimer's Disease. (US Patent No. US20140228438 A1, 2012)

The U.S. Pat. Application No. 20,060,135,599, referenced herein, discloses the invention that relates to the use of one or more CBs in the treatment of neuropathic or chronic pain. A method of treating brachial plexus avulsion in a human patient comprising administering to a patient in need thereof effective amount one or more CBs. (US Patent No. US20060135599 A1, 2003)

The U.S. Pat. No. 8,980,940, referenced herein, discloses a composition comprising a high purity CB, an acid, and a pharmaceutically-acceptable solvent that achieves room temperature stability for over 24 months. The acid improves the stability of the composition and the solvent enhances the solubility of the acid, thereby allowing the acid to have an improved stabilizing effect on the highly pure CB. Preferably, the solvent is an alcohol and, more preferably, the composition contains an oil. A method for making the composition includes combining the CB and the solvent and evaporating a portion of the solvent, along with adding an acid to the composition, before, during, or after the evaporating step. A method for making and storing the composition includes storing the composition in a manner adapted to maintain its stability. (U.S. Pat. No. 8,980,940 B2, 2011)

The U.S. Pat. Application No. 20,080,175,902, referenced herein, discloses methods for slowing the progression of MS comprising administering a therapeutically effective amount of CB to a patient suffering from MS. A method of slowing the progression of MS in a patient in need thereof, comprising administration of a pharmaceutical composition containing an effective amount of therapeutically effective CB on a regular basis; the administration occurring over a period of time: at least about 16 weeks, at least about 27 weeks, at least about 40 weeks and at least about 52 weeks. (US Patent No. US20080175902 A1, 2007)

The U.S. Pat. Application No. 20,060,167,084, referenced herein, discloses methods of, inter alia, treating and/or preventing symptoms associated with MS and its relapse. A method of treating and/or preventing symptoms associated with MS in a subject in need thereof, the method comprising administering to the subject a therapeutically effective amount of a pharmaceutical composition comprising delta-9-THC. (US Patent No. US20060167084 A1, 2005)

The U.S. Pat. Application No. 20,040,018,151, referenced herein, discloses in one aspect, a method for promoting normal motor function in Amyotrophic Lateral Sclerosis (ALS) patients. The method comprises administering a compound that is an anandamide/CB receptor/acceptor agonist to a mammal having observable motor function, and evaluating one or more indicia of motor function in said mammal, wherein a compound that promotes normal motor function is identified. More preferably, the mammal to which the administration is made has one or more ALS or Motor Neuron Disease (MND) symptoms and such one or more symptoms include at least one of the observable motor functions being evaluated. (US Patent No. US20040018151 A1, 2003)

SUMMARY OF THE INVENTION

The following description presents a simplified view of one or more aspects of the proposed invention. This summary is not an extensive overview of all contemplated embodiments and implementations. It is intended to neither identify key or critical elements of all features, nor delineate the scope of any or all facets. Its sole purpose is to present some concepts of one or more aspects in a simplified form.

A CB-containing plant extract contains in addition to one or more other CBs, one or more non-CB components which are co-extracted with the CBs from the plant material. Their respective ranges will vary according to the starting plant material and the extraction methodology used. CB-containing plant extracts may be obtained by various means of extraction of cannabis plant material. Such means include but are not limited to: supercritical or subcritical extraction with $CO_2$, extraction with hot gas, and extraction with solvents. The terms "cannabinoid-containing plant extract", or "cannabinoid extract", or "cannabis extract", or *Cannabis* plant, or similar are taken herein to refer to one or more plant extracts from any plant in the Cannabaceae family or any plant that contains any form of THC and/or CBD.

It was discovered, that the use of a cannabis extract that contains THC and CBD in the ratio of approximately 1 (THC) and 2 (CBD) by weigh, or THC and CBD in the ratio of 0.5 to 1 (THC) and 1.5 to 2 (CBD) by weight, or THC and CBD in the ratio of 1 to 1.5 (THC) and 2 to 2.5 (CBD) by weight; and in addition contains one or more other CBs and one or more non-CB components that are co-extracted with the CBs from the plant material is more effective in the treatment of hyper and hypokinetic movement symptoms in the aforementioned diseases and disorders than a medicinal extract containing pure THC.

It was also discovered that some of the unwanted side effects caused by currently available medications are reduced or eliminated by treatment with the compound disclosed herein, for example: Marinol in the case of MS, opiates in the case of cancer and trauma, Tetrabenazine and Benzodiazepine in the case of HD, and others.

In one embodiment of the proposed invention, the treatment of HD chorea involves giving to a patient in the morning by oral administration a one soft-gel capsule of the compound containing a mixture of delta-9 and delta-8-THC and the CBD in the ratio of approximately 0.7 and 2 by weigh, and such mixture contains a small amount of other CBs, and in one embodiment, one or more non-CB components, such as sesame oil, where such capsule is a time-released capsule designed to release said mixture in the small intestine; and in another embodiment, in the stomach; and in another embodiment, as exemplified in FIG. 4. The aforesaid compound and method in some subjects may reduce symptoms associated with, in one embodiment, HD chorea, having minimal to nonexistent psychotropic effect.

In another embodiment of the proposed invention, the treatment of LID, such as a common side effect of PD levodopa treatment, involves giving to a patient before bed time by oral administration a dose of medicament—in one embodiment, one extended release soft-gel capsule and one immediate release soft-gel capsule of the compound containing a mixture of delta-9-THC and CBD in the ratio of approximately 1.5 and 2 by weigh, and such mixture contains a small amount of other CBs, and in one embodiment, one or more non-CB components, such as sesame oil. This method provides effective control of symptoms at bed time with a desired mild psychotropic effect acting as a sleeping aid.

In another embodiment of the proposed invention, the treatment of MS spasticity involves giving to a patient two times a day by oral administration a dose of medicament, in one embodiment, a soft-gelatin capsule that consists of type A and/or B gelatin, water, and a plasticizer, such as glycerin or sorbitol; and encapsulates a compound containing a liquid mixture that includes: 10 mg of delta-9-THC and 20 mg of CBD, some sesame oil, some methyl and propyl parabens, some other cannabinoids and some other substances that are cumulatively less than 5% of the overall mixture, or as in one embodiment exemplified in FIG. 4.

The proposed invention provides methods and compounds for treatment of multiple diseases and disorders at various stages with different patients potentially presenting different motoric dysfunction symptoms, and as such requiring larger or smaller doses to achieve the desired efficacy. Besides, certain variations of THC/CBD ratios and other components may be required to achieve the desired effect, such as the night or day-time application.

In one aspect of the invention, titration of doses is beneficial to patients as they can take smaller doses of the medication to achieve efficacy. It is understandable that not all patients will require the same dose of medication; for example, patients of a larger build or faster metabolism may require a higher dose than that required by a patient that is of a smaller build or slower metabolism. In one embodiment said titration is adjusted with a time-release and point of release-tailored dosage forms. For instance, a gelatin capsule or a tablet designed to release medication in doses in certain parts of the digestive system to achieve the desired efficacy.

In another embodiment, the dose of medicament to be administered to a subject suffering from HD-related chorea is formulated such that a specific patient can titrate such dose; where the term "titrate" means that the patient is provided with a medication that is in such a form or engineered in such a way that smaller doses than the unit dose can be taken. In one embodiment, the titratable dosage forms are gel, gel spray, transdermal patch, liquid, vapor, spray, and the like.

The unit dosage—defined as a maximum dose of medication that can be taken at any one time or within a specified dosage period—may range, in one embodiment, between 20 and 60 mg of said medicine, or, depending on the administration route and aforesaid variables, the dosage may fluctuate significantly, such that unit dosage may consist of multiple doses taken several times a day. Administration of the compound may be carried out by any of several suitable known means, including but not limited to intraperitoneal, subcutaneous, oral, intramuscular, intravenous, and others.

These and other embodiments and objects of the invention will become apparent upon further review of the specification and claims presented herein. Thus, the above and the following expressed embodiments and objects of the invention are not intended by the inventors to limit the scope of the invention.

BRIEF DESCRIPTION OF THE DRAWINGS

The accompanying drawings, which are incorporated in and constitute a part of this specification, illustrate aspects of the present teachings and together with the description, serve to explain principles of the present teachings.

The FIG. 1, incorporated herein by reference, compares the oxidation potentials of CBs and the BHT. The oxidation profiles of (750 µM) BHT, CBs, and anandamide were compared by cyclic voltammetry. Anandamide, a CB receptor ligand with a non-CB structure, was used as a nonresponsive control. Experiments were repeated three times with essentially the same results. (Hampson, Grimaldi, Axelrod, & Wink, 1998)

Figure 1:
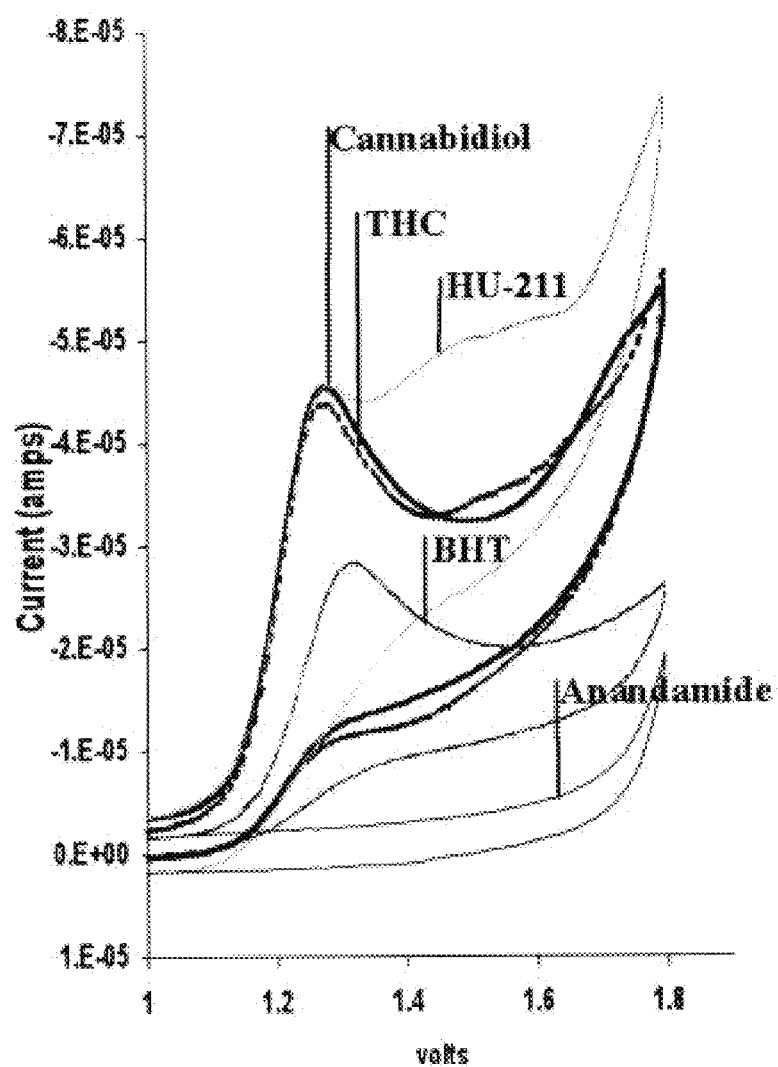
Figure 2:
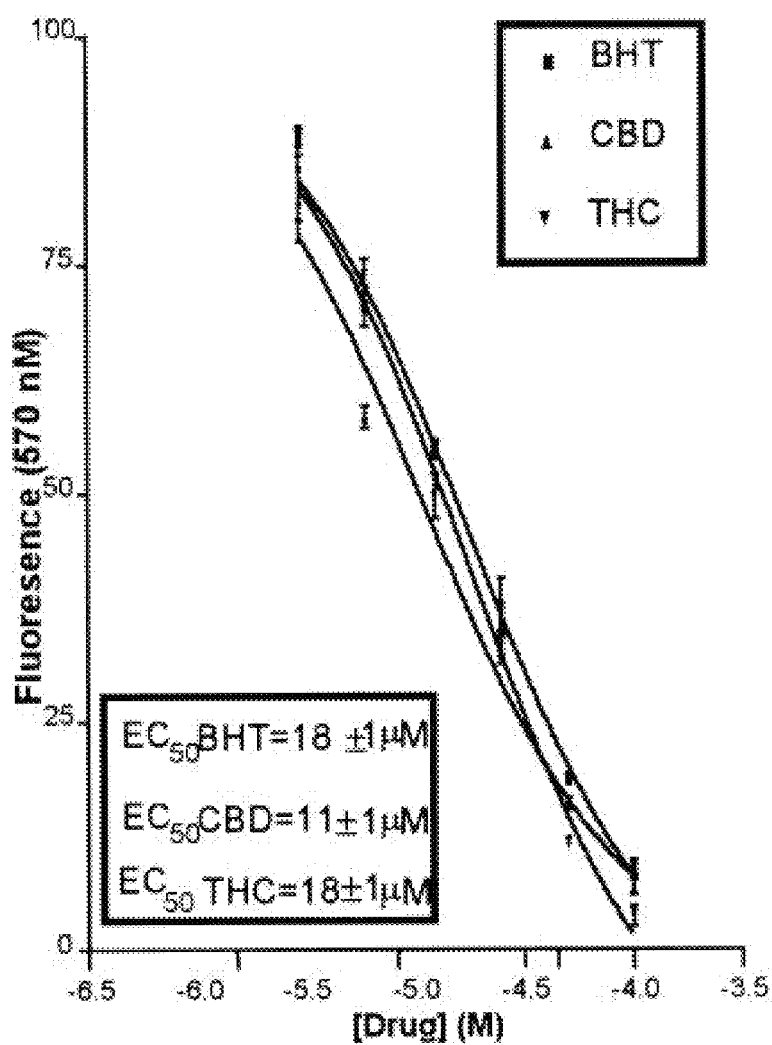

The FIG. 2, incorporated herein by reference, compares the oxidation potentials of CBs and the antioxidant BHT. Effect of CBD and THC on dihydrorhodamine oxidation. CBs were compared with BHT for their ability to prevent tert-butyl hydroperoxide-induced oxidation of dihydrorhodamine. Data represent mean values±SEM from a single experiment with three replicates. This experiment was repeated four times with essentially the same results. (Hampson, Grimaldi, Axelrod, & Wink, 1998)

The FIG. 3, incorporated herein by reference, shows the results of certain preclinical studies assessing therapeutic symptomatic efficacy of CBs for HD chorea. (Kluger, Triolo, Jones, & Jankovic, 2015)

Figure 4:
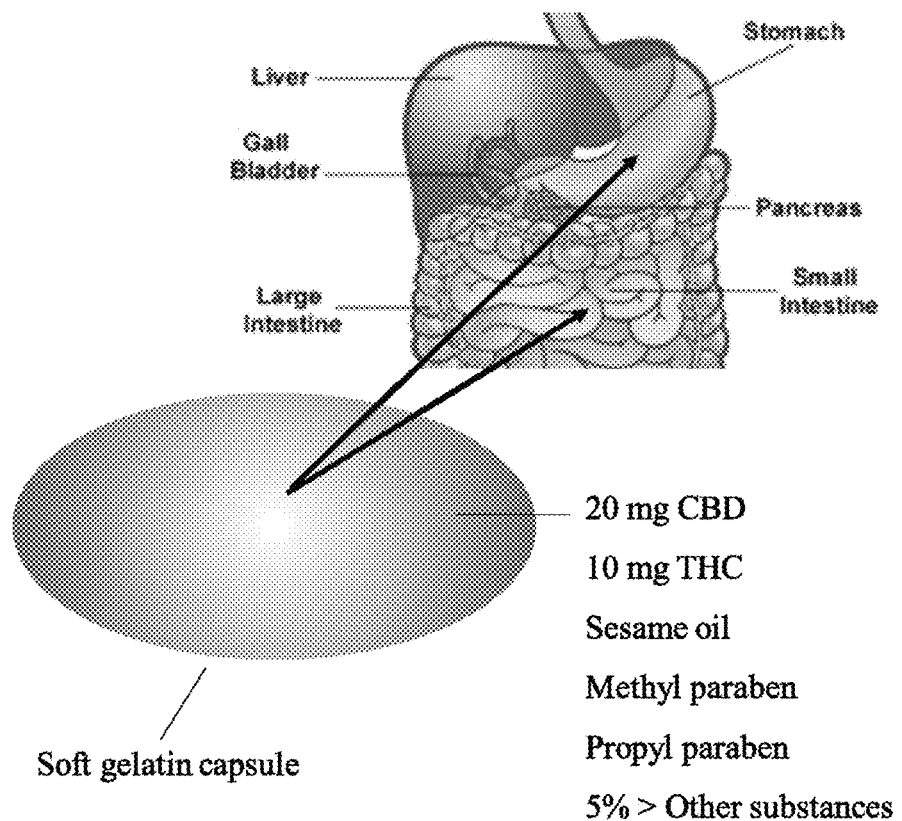

The FIG. 4, incorporated herein by reference, shows a variable-release soft-gelatin capsule pill, one of many possible dosage forms, that consists of predominantly type A or B gelatin, water, sorbitol, and encapsulates a compound containing a liquid mixture that includes: 10 mg of THC and 20 mg of CBD, some sesame oil, some methyl/propyl parabens, and less than 5% of some other CBs and some other substances.

DESCRIPTION OF EMBODIMENTS

Reference will now be made to embodiments, examples of which are illustrated in the accompanying drawings. In the following description, some details are set forth in order to provide understanding of the proposed invention. However, it will be apparent to one of ordinary skill in the art that the present invention may be practiced without these details. In other instances, well-known methods, procedures, and components have not been described in detail so as not to unnecessarily obscure aspects of the embodiments.

It will also be understood that, although the terms first, second, etc., may be used herein to describe various elements, these elements should not be limited by these terms. These terms are only used to distinguish one element from another. For example, a first contact could be termed a second contact, and, similarly, a second contact could be termed a first contact, without departing from the scope of the present invention. The first contact and the second contact are both contacts, but they are not the same contact.

The terminology used in the description of the invention herein is for the purpose of describing particular embodiments only and it is not intended to be limiting of the invention. As used in the description of the invention and the appended claims, the singular forms "a," "an," and "the" are intended to include the plural forms as well, unless the context clearly indicates otherwise. Moreover, the term "or" is intended to mean an inclusive "or" rather than an exclusive "or." That is, unless specified otherwise, or clear from the context, the phrase "X employs A or B" is intended to mean any of the natural inclusive permutations. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if is detected" may be construed to mean "upon determining" or "in response to determining" or "upon detecting (the stated condition or event)" or "in response to detecting (the stated condition or event)," depending on the context.

As used herein, the terms "related", "in connection", or "associated", or "relevant", and similar, depending on the context, means any association, whether direct or indirect, by any applicable criteria as the case may be.

The word "exemplary" is used herein to mean "serving as an example, instance, or illustration". And no aspect of this disclosure shall be construed as preferred or advantageous over other aspects or designs unless expressly stated.

CBs are compounds usually derived from *Cannabis sativa*, an annual plant in the Cannabaceae family. The plant contains more than 420 different components, with at least 61 compounds of these belonging to the class of CBs. The most active naturally occurring CBs are THC and CBD, which could possibly be used for the treatment of a wide range of medical conditions, including neuropathic pain, symptoms of hyper and hypokinetic movement diseases and disorders, fibromyalgia, and others.

The present invention provides a treatment method of certain diseases and disorders, as well as a pharmaceutical compound that represents a stable, slow and fast-acting formulations of CBs or its derivatives, prodrugs, or analogs (for the purpose of this document, may be used interchangeably). An analog herein refers to a compound that is derived from a naturally occurring CB by chemical, biological or synthetic transformation of the naturally occurring CB or a synthetic or a partially synthetically derived substance that is similar or near similar to a CB in question. According to one aspect, therefore, liquid compounds of CBs are provided in certain rations as disclosed herein.

Illustrative of CBs or CB analogues are compounds selected from the group consisting of cannabinol, cannabidiol, $\Delta 8$-tetrahydrocannabinol, $\Delta 9$-tetrahydrocannabinol, 11-hydroxy-tetrahydrocannabinol, 11-bydroxy-$\Delta 9$-tetrahydrocannabinol, levonantradol, $\Delta 11$-tetrahydrocannabinol, tetranydrocannabinol, tetrahydrocannabivarin, dronabinol, amandamide, nabilone, a combination thereof, a natural or synthetic analogue or equivalent thereof, and a natural or synthetic molecule with a basic CB structure.

The natural CB compounds are readily obtained from plant tissue by suspending the tissue in an appropriate solvent to extract CB compounds and other tissue components. Analytical purification of such an extract provides pharmaceutical grade CB compounds. Alternatively, CB compounds are extracted from plant tissue under supercritical conditions. Solvents used for supercritical extraction of CBs include, for instance: carbon dioxide, or other gases in isolation or combination with or without solvent modifiers, selected from ethanol, propanol, butanol, hexane, chloroform, dichloromethane, acetone, or any organic solvent capable of extracting CB s, and alcohol-water mixtures, such as water-ethanol or water-butanol mixtures, etc.

The present invention, in one embodiment, involves producing an extract from cannabis plant matter, containing THC, CBD and optionally the carboxylic acids thereof. In one embodiment, the dried plant matter is ground and subjected to a CO2 extraction and the primary extract obtained is separated. Specifically, ground *Cannabis* plant material is compressed and charged into an extraction vessel. CO2 is then introduced, having been brought to a temperature, in one embodiment, of approximately 60° C. and to a pressure of approximately 250 bars. When the CO2 enters into contact with the material to be extracted, it extracts the desired CB components, in particular comprising $\Delta 9$-THC and CBD, as well as the carboxylic acids thereof. In one embodiment, the extraction method permits extracting various isomers of THC, selectively obtained from industrial hemp and from drug-producing hemp, also separating undesirable waxes and removing the solvent.

CBs, including THC, can be isolated from *Cannabis* plants using the CO2 extraction or any other extraction method, or can be made semi-synthetically. It is preferable, in one embodiment, that the extraction/production method yields substantially the (-)-$\Delta^9$-trans-THC isomer that is the most active isomer of THC. There are also various techniques that are known for isolating and separating the (-)-$\Delta^9$-trans-THC isomer from other compounds in THC. For example, U.S. Pat. No. 7,449,589 describes methods for purifying the (-)-$\Delta^9$-trans-THC isomer from a mixture of other THC isomers. (U.S. Pat. No. 7,449,589 B2, 2004)

However, THC, and in particular the (-)-$\Delta^9$-trans-THC isomer, is very unstable. Also, chemical synthesis and isolation of (-)-$\Delta^9$-trans-THC are both challenging. The (-)-$\Delta^9$-trans-THC isomer is very prone to acid-catalysed isomerization to the $\Delta^8$-THC isomer, is easily oxidized by oxygen to form inactive cannibinol, and is also sensitive to light and heat. All of these factors make it difficult to synthesize, purify, and store a high purity THC compound comprising the (-)-$\Delta^9$-trans-THC isomer which is stable over time and under various storage conditions.

It is not the purpose of present disclosure to provide particulars concerning the attainment of a colloidal formulation that is stable under a range of conditions. Though, in one embodiment, the disclosed compound with initial purity (HPLC) of THC and CBD being at least 98% by area can achieve stability such that at least 95% by area remains in undegraded form after exposure of the compound to the storage conditions for twelve months, where the ambient temperature is between 20° C. and 40° C. and relative humidity is between 55% and 75%.

In one embodiment, the stability of said compound is attained by contacting a solution containing CBs into a solvent such as water, $C1$-$C_6$ aliphatic alcohols, or mixtures of water and alcohols, acetone, or other water-miscible organic solvents that can be used to dissolve the CBs; and in another embodiment, with addition of pharmaceutically acceptable buffers, stabilizers, and other pharmacologically inactive substances.

In one embodiment, the inventive CB compound is in the form of micelles or liposomes that encapsulate a CB within the membrane of the micelles or liposomes. Within the context of the present technology, the term "micelle" refers to an aggregate of surfactant molecules dispersed in a liquid colloid, while "liposome" refers to a vesicle composed of a mono or bilayer lipid.

In yet another embodiment, other drugs and pharmaceutically acceptable carriers, if present, may be in the lipophilic membrane or entrapped in the aqueous fluid that forms the core of the liposome. The entrapped CBs contribute to the stability of the micelle/liposome membranes, such that the micelle/liposomes formulations may be used as an improved, fast, reliable and efficient system for the oral, enteral, parenteral, intravenous or topical delivery of CBs and/or additional drugs to subjects in need thereof. The term "subject" or "patient" refers to a mammal in need of treatment or undergoing treatment using the inventive compounds described herein. Mammalian subjects include without limitation humans, dog, cat, horse or any other animal in need of treatment.

In another embodiment, unilamellar micelles or liposomes that are thermostable at temperatures greater than 50° C. are used in the manufacture of CB compound, according to the present invention. These micelles or liposomes are obtained by contacting a solution of CB (a CB plant extract) with an aqueous solvent or an aqueous solution of a pharmaceutically active compound or drug. The mixing of CB solution occurs in a manner suitable for the rapid dissolution of CB solution in the aqueous solution. This can be accomplished through a variety of means, including dilution, injection through a small orifice under pressure, and ultrasonic atomization.

And yet in another embodiment, the disclosed compound has advantageous properties, where the micellar and liposomal compound is stable at high temperatures, exceeding 50° C., is stable to sonication, capable of carrying large payloads of CBs as well as other drugs suitable for use in combination therapy and can be stored for extended periods of time, for example greater than 20 weeks at 25° C.

In certain embodiments, said compound can be in the form of a concentrated, stable colloidal suspension that is obtained by infusing a solvent solution containing the CB plant extract or pure CBs into a solvent such as water, with or without buffer. Stabilizing agent, for instance, a polymer or compounds selected from cellulose hyaluronic acid, polyvinyl pyrrolidone (PVP), alginate, chondritin sulfate, poly gamma glutamic acid, gelatin, chitisin, corn starch and flour can be used to stabilize the micelle formulations.

In one embodiment, said compound also exhibits superior systemic delivery and release of CBs from the micelle or liposomes used in the manufacture of the inventive compound. The release of a CB from a liposome or micelle of the inventive compound can be modulated by changing the ratio of the concentration of lipid to the concentration of CB present in the liposome.

In one embodiment, tissue specific delivery can be achieved by modifying the surface of the liposomes or micelles with compounds that bind specifically to biological macromolecules expressed on cellular surfaces. For instance, the micelle or liposomal surface can be derivatized to display an antibody specific to an antigen expressed on cancer cells.

According to one embodiment, said compound that is used in the treatment of a disease condition is administered to a patient or subject in need of treatment either alone or in combination with other compounds/drugs having similar or different biological activities. For example, said compound may be administered in a combination therapy, i.e., either simultaneously in single or separate dosage forms or in separate dosage forms within hours or days of each other. Examples of compounds/drugs used in such combination therapies include without limitation: chemotherapeutic agents, immunosuppressive agents, immunostimulatory, anti-pyretic, cytokines, opioids, cytokines, cytotoxic agents, nucleolytic compounds, radioactive isotopes, receptors, pro-drug activating enzymes, which may be naturally occurring or produced by recombinant methods, anti-inflammatory agents, antibiotics, protease inhibitors, growth factors, osteo-inductive factors and the like.

In some embodiments, the compound further contains, in accordance with accepted practices of pharmaceutical compounding, one or more pharmaceutically acceptable excipients, including without limitation: diluents, adjuvants, stabilizers, emulsifiers, preservatives, colorants, buffers, flavor imparting agents. As stated above, said compound may contain a CB, a CB analog or both, and may be consumed directly or formulated into nutraceutical or pharmaceutically acceptable compounds suitable for oral, enteral, parenteral, intravenous, topical, or other administration.

The term "parenteral" as used herein includes subcutaneous injections, intravenous, intramuscular, intrasternal injection or infusion techniques. Such excipients are well known in the art. Dosage forms for oral administration include food, beverages, drinks, soups, baked goods, syrups, oral pharmaceutical compounds, nutraceutical formulations, and the like. Suitable pharmaceutical carriers include any such materials known in the art, e.g., any liquid, gel, solvent, liquid diluent, solubilizer, polymer or the like, which do not significantly interact with other components of the formulations in a deleterious manner.

Liquid dosage forms for oral administration include, but are not limited to, pharmaceutically acceptable emulsions, solutions, suspensions, syrups and elixirs. In addition to the CB plant extract, the liquid dosage forms may contain inert diluents commonly used in the art. For instance, liquid formulations can contain water, alcohol, polyethylene glycol ethers, and any other pharmaceutically acceptable solvents. Solubilizing agents and emulsifiers such as, without limitation: ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols, fatty acid esters of sorbitan and mixtures thereof may also be present in said compound.

Additionally, oral compound of the proposed invention can include, without limitation, adjuvants such as wetting agents, emulsifying and suspending agents, sweetening, flavoring, coloring, and perfuming agents. When formulated as a suspension, said compound may contain the CB plant extract and suspending agents, for example, without limitation: ethoxylated isostearyl alcohols, polyoxyethylene sorbitol, sorbitan esters, microcrystalline cellulose, aluminum metahydroxide, bentonite, agar-agar, tragacanth, and mixtures thereof.

In one embodiment, the emulsifier may comprise a mixture of monoglyceride and diglyceride at a total concentration of 1% to 99% w/w and a carrageenan or mixture of carrageenans at a total concentration of 0.01% to 10% w/w, in another embodiment, no carrageenans may be present. In another embodiment, the emulsifier may be present in a concentration range of 1% to 99%, 5% to 80%, 10% to 35%, 10% to 20%, or about 15%-25%% w/w.

Solid dosage forms suitable for oral administration include, capsules, tablets, pills, powders, and granules. In such solid dosage forms, the CB extract can be used alone or in combination with one or more drugs that are mixed with at least one pharmaceutically acceptable excipient or carrier such as sodium citrate or dicalcium phosphate, and/or fillers or extenders such as starches, lactose, sucrose, glucose, mannitol, and silicic acid; binders such as, for example, carboxymethylcellulose, alginates, gelatin, polyvinylpyrrolidone, sucrose, and acacia; humectants such as glycerol; disintegrating agents such as agar-agar, calcium carbonate, potato or tapioca starch, alginic acid, certain silicates, and sodium carbonate; solution retarding agents such as paraffin; absorption accelerators such as quaternary ammonium compounds; wetting agents such as, for example, acetyl alcohol and glycerol monostearate; absorbents such as kaolin and bentonite clay; and lubricants such as talc, calcium stearate, magnesium stearate, solid polyethylene glycols, sodium lauryl sulfate, and mixtures thereof. For capsules, tablets and pills, in one embodiment, the dosage form can also comprise buffering agents.

Micellular or liposomal suspensions can be encapsulated with a variety of polymers, sugars, and chelating agents, to yield stable solid liposomal CB preparation. Encapsulation can take the form of crosslinked polymers, trapping of the micells or liposomes within a non-crosslinked polymer network, or dispersed within the crystalline structure of sugar starches or protein molecules. These granules can be further processed to yield sublingual films, suppositories, dispersible powder, tablets, gel capsules, and so forth.

Solid dosages in the form of tablets, capsules, pills, and granules, in one embodiment, can be coated using compounds that accelerate or decrease the release of CBs. For instance, the proposed invention also encompasses solid dosage forms having enteric coatings, extended-release coatings, sustained-release coatings, delayed release coatings and immediate-release coatings. Methods used to coat solid dosage forms as well as the materials used to manufacture such coatings are well known in the pharmaceutical formulary art. The solid dosage forms can optionally contain opacity enhancing agents. According to an embodiment, the solid dosage form comprises an enteric coating that permits the release of a CB or a CB analog alone or in combination with one or more drugs at a specific location within the gastrointestinal tract, optionally, in a delayed manner. Exemplary of such coating materials include glyceryl monostearate or glyceryl distearate may be employed, polymeric substances and waxes. The CB plant extract, for instance, can be provided alone or in combination with one or more drugs that can also be in micro-encapsulated form, if appropriate, with one or more of the above-mentioned excipients.

In one embodiments, said compound is packaged into a gelatin capsule dosage form. In another embodiment, the compound is packaged into a non-gelatin capsule or an HPMC capsule. Said capsule can be a vegan based capsule or else. The compound disclosed herein includes a sustained release compound, an immediate release compound, or a combined sustained release fraction and immediate release fraction. In one embodiment, the therapeutic effect of the compound has a duration up to 2 hours, up to 4 hours, up to 6 hours, up to 8 hours, up to 10 hours, up to 12 hours, up to 14 hours, up to 16 hours, up to 18 hours, or up to 24 hours. In one embodiment, the compound disclosed herein comprises an immediate release fraction and a sustained release fraction, wherein the immediate release fraction comprises a therapeutically effective amount of CBs and an edible oil; and wherein the sustained release fraction comprises a therapeutically effective amount of CBs, and a mixture of emulsifiers and other pharmacologically inactive substances.

In another embodiment, a dietary compound, according to the present invention, is any ingestible preparation that contains the CB suspensions of the invention mixed with a food product. The food product can be dried, cooked, boiled, lyophilized or baked. Breads, teas, soups, cereals, salads, sandwiches, sprouts, vegetables, animal feed, pills and tablets, are among the vast number of different food products contemplated in the present invention.

In yet another embodiment, a compound for parenteral injection comprises pharmaceutically acceptable sterile aqueous or non-aqueous solutions, dispersions, suspensions or emulsions as well as sterile powders for reconstitution into sterile injectable solutions or dispersions prior to use. Examples of suitable aqueous and non-aqueous carriers, diluents, solvents or vehicles include, without limitation, water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate.

In one embodiment, proper fluidity can be maintained, for example, by the use of coating materials such as lecithin, by the maintenance of the required particle size in the case of dispersions, and by the use of surfactants. The compound of the present invention can also contain adjuvants such as, but not limited to, preservatives, wetting agents, emulsifying agents, and dispersing agents. The compound for parenteral delivery generally includes isotonic agents such as sugars, sodium chloride, and the like. Prolonged absorption of the injectable pharmaceutical formulation can be brought about by the inclusion of agents which delay absorption such as aluminum monostearate and gelatin.

Injectable depot forms are made by forming microencapsule matrices of the drug in biodegradable polymers such as polylactide-polyglycolide. Depending upon the ratio of drug to polymer and the nature of the specific polymer employed, the rate of drug release can be controlled. Examples of other biodegradable polymers include poly-orthoesters and polyanhydrides. Depot injectable formulations are also prepared by entrapping the drug in liposomes or microemulsions which are compatible with body tissues. The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Dosage forms for topical administration include, but are not limited to, ointments, creams, emulsions, lotions, gels, sunscreens and agents that favor penetration within the epidermis. Various additives, known to those skilled in the art, may be included in the topical formulations of the invention. Examples of additives include, but are not limited to, solubilizers, skin permeation enhancers, preservatives (e.g., anti-oxidants), moisturizers, gelling agents, buffering agents, surfactants, emulsifiers, emollients, thickening agents, stabilizers, humectants, dispersing agents and pharmaceutical carriers. Examples of moisturizers include jojoba oil and evening primrose oil.

Suitable skin permeation enhancers are well known in the art and include lower alkanols, such as methanol ethanol and 2-propanol, alkyl methyl sulfoxides such as dimethylsulfoxide (DMSO), decylmethylsulfoxide (C10 MSO) and tetradecylmethyl sulfoxide; pyrrolidones, urea; N,N-diethyl-m-toluamide; C2-C6 alkanediols; dimethyl formamide (DMF), N,N-dimethylacetamide (DMA) and tetrahydrofurfuryl alcohol. Examples of solubilizers include, but are not limited to, hydrophilic ethers such as diethylene glycol monoethyl ether and diethylene glycol monoethyl ether oleate; polyoxy 35 castor oil, polyoxy 40 hydrogenated castor oil, polyethylene glycol (PEG), particularly low molecular weight PEGs, such as PEG 300 and PEG 400, and polyethylene glycol derivatives such as PEG-8 caprylic/capric glycerides; alkyl methyl sulfoxides, such as DMSO; pyrrolidones, DMA, and mixtures thereof.

Prevention and/or treatment of infections can be achieved by the inclusion of antibiotics, as well as various antibacterial and antifungal agents, for example, paraben, chlorobutanol, phenol sorbic acid, and the like, in the compounds of the invention.

One of ordinary skill will appreciate that effective amounts of the agents in the compound used in the methods of the invention can be determined empirically. It will be understood that, when administered to a subject, the total daily usage of the compound of the present invention will be decided by the attending physician within the scope of sound medical judgment. The specific therapeutically effective dose level for any patient will depend upon a variety of factors: the type and degree of the response to be achieved; the activity of the specific compound employed; the age, body weight, general health, sex and diet of the patient; the duration of the treatment; drugs used in combination or coincidental with the method of the invention; and like factors well known in the medical arts.

The formulations of the invention, in one embodiment, are therefore particularly suitable for oral administration and may be administered to subjects with a pre-existing condition or pre-disposed to certain disease conditions, such as without limitations: autoimmune diseases and disorders, motor neuron diseases and disorders, neurodegenerative diseases and disorders, pain associated with cancer and trauma; and other conditions, as contemplated by the invention, that include, but are not limited to: HD; Wilson's Disease; Sydenham's Chorea; Chorea Gravidarum; Autosomal Dominant Neurogenetic Syndrome; Huntington's Disease-Like Syndrome; Prion Disease; Spinocerebellar Ataxias; Neuroacanthocytosis; Dentatorubral-Pallidoluysian Atrophy; Brain Iron Accumulation Disorders; Friedreich's Ataxia; Mitochondrial Disease; Rett Syndrome; Cerebrovascular Disease; PANDAS; LID; anti-convulsants and anti-psychotics drugs-related symptoms; Systemic Lupus Erythematosus; Antiphospholipid Syndrome; TS; Thyrotoxicosis; Polycythaemia Rubra Vera; Spongiform Encephalopathies; Coeliac Disease; PD; metabolic and endocrine-related diseases and disorders; athetosis-related to damage or degeneration of basal ganglia; minor tranquilizers and alcohol withdrawal syndromes; symptoms or side effects associated with anti-retroviral therapy, chemotherapy and radiation therapy.

In one embodiment of the proposed invention, the treatment of symptoms of motor neuron diseases involves giving to a patient in the morning by oral administration a one soft-gel capsule of the compound containing a mixture that includes THC and CBD in the ratio of approximately 0.9 (THC) and 2 (CBD) by weigh, and such mixture contains some amount of other CBs, and in one embodiment, one or more non-CB components, such as sesame oil, where such capsule is a time-released capsule designed to release said mixture in the small intestine; and in another embodiment, in the stomach. The aforesaid compound and method in some subjects may reduce symptoms associated with, in one embodiment, Wilson's Disease, having minimal to nonexistent psychotropic effect.

In another embodiment of the proposed invention, the treatment of benzodiazepine withdrawal symptoms involves giving to a patient before bed time by oral administration a dose of medicament, in one embodiment, one extended release gelatin capsule and one immediate release soft-gelatin capsule of the compound containing a mixture of THC and CBD in the ratio of approximately 1.8 (THC) and 1.5 (CBD) by weigh, and such mixture contains a small amount of other CBs, and in one embodiment, one or more non-CB components, such as sesame oil. This method provides effective control of symptoms at bed time with a moderate psychotropic effect acting as a sleeping aid.

In another embodiment of the proposed invention, the treatment of TS symptoms involves giving to a patient two times a day by oral administration a dose of medicament, in one embodiment, a soft-gelatin capsule that consists of some type B and/or type A gelatin, water, and a plasticizer, such as glycerin; and encapsulates a compound containing a liquid mixture that includes: 15 mg of THC or THC analog, 20 mg of CBD or CBD analog, some sesame oil, some methyl and propyl parabens, some other cannabinoids, and less than 20% of other substances.

The potential commercial uses of the disclosed preparations include, for example, protective/prophylactic and medical uses. The compounds of the invention can also be administered by a variety of other routes, including mucosal, subcutaneous and intramuscular administration, and may comprise a variety of carriers or excipients known in the formulary art, such as, non-toxic solid, semisolid or liquid filler, diluent, encapsulating material and formulation auxiliaries that are pharmaceutically acceptable.

The features disclosed in the foregoing description, or the following claims, or the accompanying drawings, expressed in their specific forms or in terms of a means for performing the disclosed function, or a method or system for attaining the disclosed result, as appropriate, may separately, or in any combination of such features, be utilized for realizing the invention in diverse forms thereof.

While various embodiments of the present invention have been described above, it should be understood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined in accordance with the following claims and their equivalents.

REFERENCES

Abood, M. (2003). US Patent No. US20040018151 A1.

Dudley, R. (2005). US Patent No. US20060167084 A1.

Formukong, E. A., Evans, A. T., & Evans, F. J. (1988, August). Analgesic and antiinflammatory activity of constituents of *Cannabis sativa L. PubMed,* 12(4), 361-371.

Geiser, F. O., Keenan, J. J., & Ros, R. (2004). U.S. Pat. No. 7,449,589 B2.

Geiser, F., Keenan, J., Rossi, R., Sanchez, A., & Whelan, J. (2004). U.S. Pat. No. 7,449,589 B2.

Guy, G., & Platt, B. (2007). U.S. Pat. No. 8,673,368 B2.

Guy, G., & Platt, B. (2014). U.S. Pat. No. 9,205,063 B2.

Guy, G., & Robson, P. (2005). U.S. Pat. No. 7,968,594 B2.

Haberstick, B., Young, S., Zeiger, J., Lessem, J., Hewitt, J., & Hopfer, C. (2014). *Prevalence and correlates of alcohol and cannabis use disorders in the United States: results from the national longitudinal study of adolescent health*. US National Library of Medicine, National Institutes of Health. doi: 10.1016/j drugalcdep.2013.11.022

Hampson, A. J., Grimaldi, M., Lolic, M., Wink, D., Rosenthal, R., & Axelrod, J. (2000).

Neuroprotective antioxidants from marijuana. *PubMed,* 274-282.

Hampson, A. J., Grimaldi, M., Axelrod, J., & Wink, D. (1998, Jul. 7). Cannabidiol and (-)Δ9-tetrahydrocannabinol are neuroprotective antioxidants. *Medical Sciences,* 95(14), pp. 8268-8273.

Iuvone, T., Di Marzo, V., Guy, G., Wright, S., & Stott, C. (2012). US Patent No. US20140228438 A1.

Kluger, B., Triolo, P., Jones, W., & Jankovic, J. (2015). *The Therapeutic Potential of Cannabinoids for Movement Disorders*. PubMed Central. doi:10.1002/mds.26142

Kottayil, G., Zhu, Z., & Gosko, V. R. (2005). U.S. Pat. No. 8,628,796 B2.

Lastres-Becker, I., Fezza, F., Cebeira, M., Bisogno, T., Ramos, J., Milone, A., . . . Di Marzo, V. (2001). *Changes in endocannabinoid transmission in the basal ganglia in a rat model of Huntington's disease*. Madrid: Universidad Complutense. Retrieved from https://www.ncbi.nlm.nih.gov/pubmed/11447320/

Meinck,H., Schönle, P., & Conrad, B. (1989). *Effect of cannabinoids on spasticity and ataxia in multiple sclerosis*. Gottingen: University of Gottingen. Retrieved from https://www.ncbi.nlm.nih.gov/pubmed/2709054/

Meschler, J., Howlett, A., & Madras, B. (2001). *Cannabinoid receptor agonist and antagonist effects on motor function in normal and 1-methyl-4-phenyl-1,2,5,6-tetrahydropyridine (MPTP)-treated non-human primates*. St. Louis: Department of Psychocological and Physiological Science, Saint Louis University. Retrieved from https://www.ncbi.nlm.nih.gov/pubmed/11465637/

Müller-Vahl, K., Kolbe, H., Schneider, U., & Emrich, H. (1998). *Cannabinoids: possible role in patho-physiology and therapy of Gilles de la Tourette syndrome*. Hannover: Department of Clinical Psychiatry and Psychotherapy, Medical School Hannover. Retrieved from https://www.ncbi.nlm.nih.gov/pubmed/9879795/

Romero, J., & Orgado, J. (2009). *Cannabinoids and neurodegenerative diseases*. Alcorcón: CIBERNED.

Rossi, R., Silverberg, L., Hoga, R., & Shah, R. M. (2011). U.S. Pat. No. 8,980,940 B2.

Sagredo, O., García-Arencibia, M., de Lago, E., Finetti, S., Decio, A., & Fernández-Ruiz, J. (2007). *Cannabinoids and neuroprotection in basal ganglia disorders*. Madrid: Universidad Complutense. doi:10.1007/s12035-007-0004-3

Symonds, C., & Berman, J. (2003). US Patent No. US20060135599 A1.

Warner, L., Kessler, R., Hughes, M., Anthony, J., & Nelson, C. (1995). *Prevalence and correlates of drug use and dependence in the United States. Results from the National Comorbidity Survey*. Ann Arbor: University of Michigan. Retrieved from https://www.ncbi.nlm.nih.gov/pubmed/7872850/

Zajicek, J. (2007). US Patent No. US20080175902 A1.

What claimed is:

1. A time release capsule consisting essentially of *cannabis*, micelles, methyl paraben, and glycerin.

2. A time release capsule consisting essentially of *cannabis*, micelles, ethyl paraben, and glycerin.

* * * * *